US006846330B2

(12) United States Patent
Yamauchi et al.

(10) Patent No.: US 6,846,330 B2
(45) Date of Patent: Jan. 25, 2005

(54) ARTIFICIAL DURA MATER AND PROCESS FOR PRODUCING DURA MATER

(75) Inventors: Koji Yamauchi, Ayabe (JP); Yoshito Ikada, Uji (JP); Susumu Miyamoto, Kyoto (JP); Keisuke Yamada, Toyonaka (JP); Tomohiko Asahara, Koto-ku (JP)

(73) Assignee: Gunze Limited, Kyoto (JP)

(*) Notice: Subject to any disclaimer, the term of this patent is extended or adjusted under 35 U.S.C. 154(b) by 161 days.

(21) Appl. No.: 10/310,521

(22) Filed: Dec. 5, 2002

(65) Prior Publication Data

US 2003/0132546 A1 Jul. 17, 2003

Related U.S. Application Data

(63) Continuation of application No. 09/529,073, filed as application No. PCT/JP98/04488 on Oct. 5, 1998, now Pat. No. 6,514,291.

(30) Foreign Application Priority Data

Oct. 6, 1997 (JP) .............................................. 9-290347

(51) Int. Cl.⁷ ............................... A61F 2/02; C08L 6/08
(52) U.S. Cl. ...................... 623/23.72; 523/113; 606/151
(58) Field of Search ........................... 623/11.11, 23.72, 623/66, 901; 600/37; 523/113, 115; 525/450; 606/151, 154

(56) References Cited

U.S. PATENT DOCUMENTS

| 4,045,418 | A | * | 8/1977 | Sinclair | 528/357 |
| 4,596,839 | A |  | 6/1986 | Peters | 523/175 |
| 5,250,584 | A | * | 10/1993 | Ikada et al. | 523/114 |
| 5,547,722 | A |  | 8/1996 | Uehara et al. | 428/35.7 |
| 5,576,584 | A |  | 11/1996 | Kusumoto et al. | 310/45 |
| 6,410,649 | B1 |  | 6/2002 | Oda et al. | 525/191 |

FOREIGN PATENT DOCUMENTS

| EP | 0734736 | 10/1996 |
| JP | 09140785 | 6/1997 |
| JP | 00080344 | 3/2000 |
| WO | 8904674 | 6/1989 |

OTHER PUBLICATIONS

"Glossary of Technical Terms in Japanese Industrial Standards, 5th Edition," p. 1296, and a translation of the definition of the term "loss factor."

"Japanese Industrial Standards—Testing methods for water resistance of textiles—JIS L1092," 1998, pp. 1–4 and 11.

English translation of "Japanese Industrial Standards—Testing methods for water resistance of textiles—JIS L1092," 1998, pp. 1–4 and 11.

Yamada, K., et al., "Development of a dural substitute from synthetic bioabsorbable polymers," *Journal of Neurosurgery*, vol. 86, No. 6 (1997), pp. 1012–1017.

San Galli, F., et al., "Use of a biodegradable elastin–fibrin material, Neuroplast®, as a dural substitute," *Biomaterials*, Elsevier Science Publishers Bv., Barking, UK, vol. 17, No. 11 (1996), pp. 1081–1085.

Noshinkeigeka; 21(2), 167–170 91993).

Journal of Biomedical Materials Research; vol. 25, pp. 267–276 (1991).

No to Shinhei; 21, pp. 1089–1098 (1969).

(List continued on next page.)

*Primary Examiner*—David J. Isabella
(74) *Attorney, Agent, or Firm*—Baker Botts LLP

(57) ABSTRACT

The present invention provides an artificial dura mater characterized by comprising at least a sheet of a biodegradable and bioabsorbable synthetic polymer and having a storage modulus at ordinary temperature of from $1 \times 10^7$ to $5 \times 10^8$ (Pa); and a process for producing an artificial dura mater characterized by dissolving a lactide/ε-caprolactone copolymer (in a molar ratio ranging from 40/60 to 60/40) in a solvent, filtering the resultant solution and casting the same followed by air drying.

9 Claims, 4 Drawing Sheets

OTHER PUBLICATIONS

Shinichiro Morita et al., "Artificial Dura Matter" JP8080344 (abstract in English) [retrieved on Sep. 15, 2003] Retrieved from the Internt: <URL: http://ep.espacenet.com/>.

Tsuguyoshi Taira et al., "Artificial Dura Matter" JP8080344 (abstract in English) [retrieved on Oct. 3, 2003] Retrieved from the Internt: <URL: http://www19.ipdl.jpo.go.jp/PA1/cgi-bin/PA1INDEX>.

Noshinkeigeka; 21(2), 167–170 (1993).

Takayama et al., 1993, "Creutzfeldt–Jakob Disease," Neurological Surgery, vol. 21, No. 2.

Collins et al., 1991, "Use of collagen film as a dural substitute: Preliminary animal studies" Journal of Biomedical Materials Research vol. 25, pp. 267–276.

Mizazaki et al., 1969, "Fundamental and Clinical Studies on the Absorbable Gelatin Film as Dural Substrate," Handbook of Clinical Neurology, No to Shinhei; 2, pp. 1089–1098.

"Glossary of Technical Terms in Japanese Industrial Standards, 5th Edition," p. 1296, and a translation of the definition of the term "loss factor."

* cited by examiner

# ARTIFICIAL DURA MATER AND PROCESS FOR PRODUCING DURA MATER

CROSS-REFERENCE TO RELATED APPLICATIONS

This application is a continuation of U.S. patent application Ser. No. 09/529,073, filed Apr. 6, 2000, now U.S. Pat. No. 6,514,291 which is a national phase application of International Application No. PCT/JP98/04488 which was filed on Oct. 5, 1998 and which published in Japanese on Apr. 15, 1999, which in turn claims priority from Japanese Application Number 290347/1997, which was filed on Oct. 6, 1997.

TECHNICAL FIELD

The present invention relates to an artificial dura mater to be used for prosthesis of dural defect in the field of neurosurgery and a process for producing the same.

BACKGROUND ART

The dura mater, occurring between the cranial bones and brain and covering the spinal cord, protects the brain and spinal cord and inhibits leakage of cerebrospinal fluid. In the field of neurosurgery, a defect or contracture of the dura mater used to be filled with lyophilized products of human dura mater.

However, the lyophilized products of human dura mater have had drawbacks such as low homogeneity and short supply. Further, a possible transmission of infection of Creutzfelt-Jacob disease through the use of the human dura mater was reported (Noshinkeigeka; 21(2), 167–170, 1993) and, eventually, the Japanese Ministry of Health and Welfare banned the use of the lyophilized product of human dura mater on Apr. 7, 1997.

To solve the above drawbacks, artificial dura mater made of silicone, for example, was developed. However, the silicone dura mater has fallen into disuse as it was reported that the silicone dura mater predisposed to meningorrhagia by remaining in vivo permanently because it was non-biodegradable, whereby being a chronic stimulant for the surrounding tissue to cause hypertrophy of the granulation tissue.

In contrast, artificial dura maters made of biodegradable and bioabsorbable materials such as collagen (*Journal of Biomedical Materials Research*; Vol. 25, 267–276, 1991) and gelatin (No to Shinkei; 21 1089–1098, 1969) were produced, but they were not in practical use because of strength-related problems, i.e., because of the insufficiency in the suture strength to be sutured integrally with the internal dura mater.

The applicant provided, in Japanese Unexamined Patent Publication No. 8-80344, an artificial dura mater comprising a sheet made of a biodegradable and bioabsorbable polymer, for example, a copolymer of lactic acid and caprolactone and, further, an artificial dura mater comprising introducing a biodegradable and bioabsorbable polymer made of a material different from that of the sheet as a reinforcement between the sheets and integrally molding the sheets and the reinforcement.

The present invention relates to improvements in the artificial dura mater disclosed in the above publication. An object of the present invention is to provide an artificial dura mater improved in qualities such as non-leakage and suture strength, and a process for producing the same.

DISCLOSURE OF INVENTION

Figure 1:
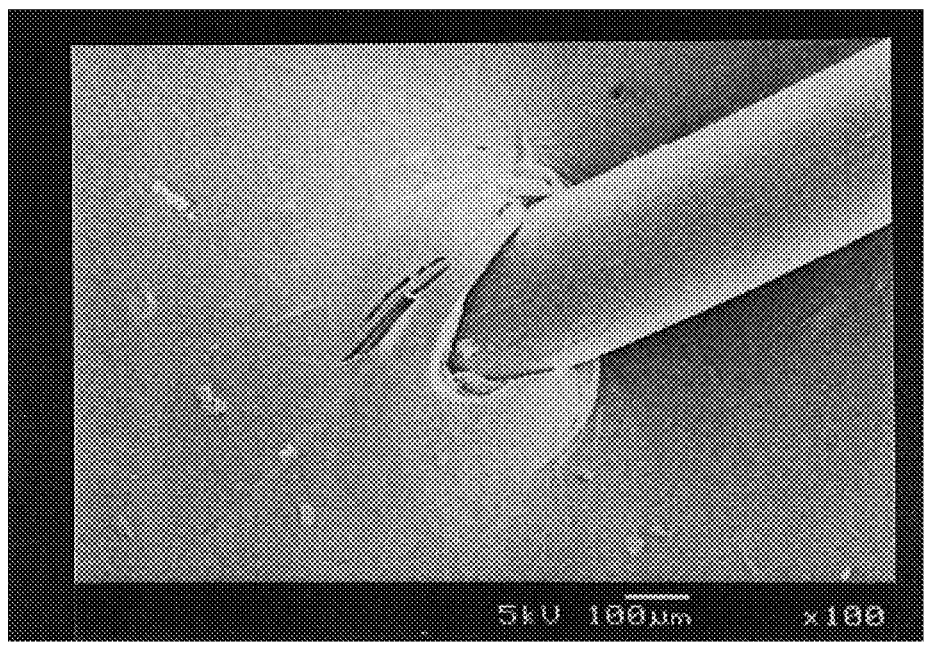
FIG. 1 is a photograph of the artificial dura mater of the invention obtained in Example 1 with a suture passed therethrough.
Figure 2:
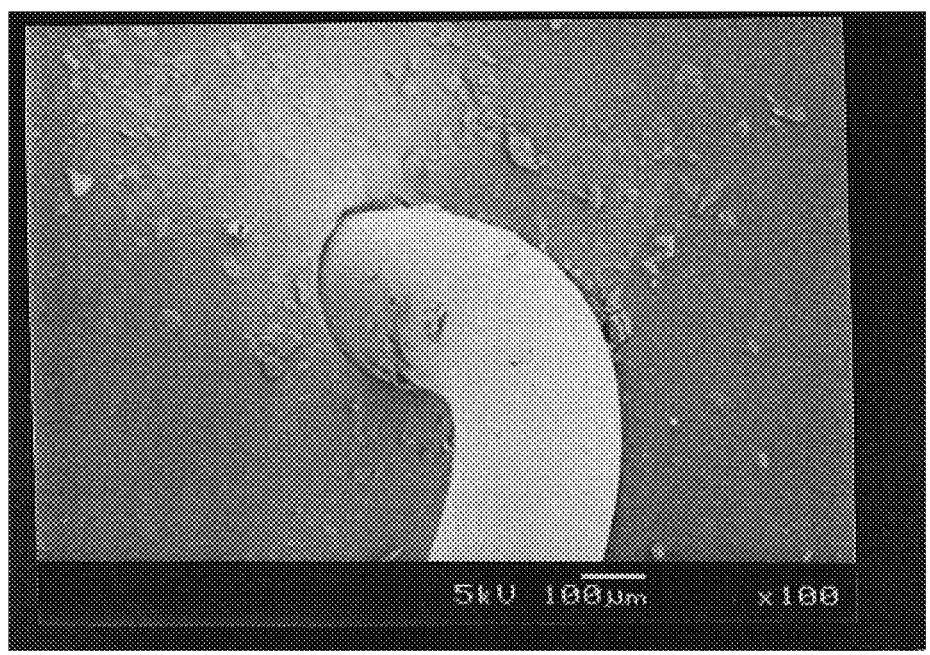
FIG. 2 is a photograph of the artificial dura mater of the invention obtained in Example 2 with a suture passed therethrough.
Figure 3:
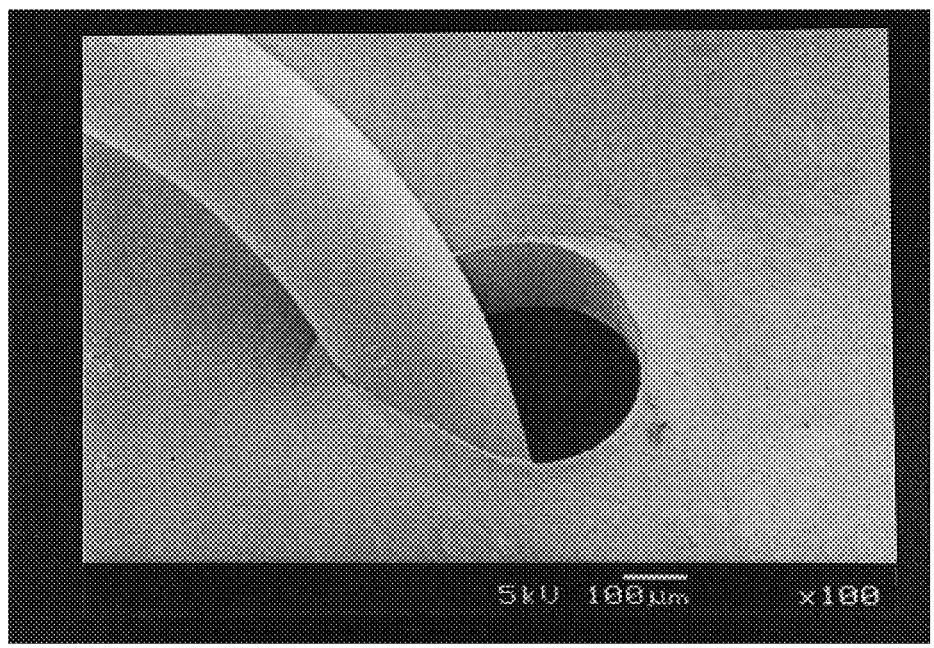
FIG. 3 is a photograph of an e-PTFE manufactured by W. L. Gore & Associates, Inc. (GORE-TEX (registered trademark)) with a suture passed therethrough.
Figure 4:
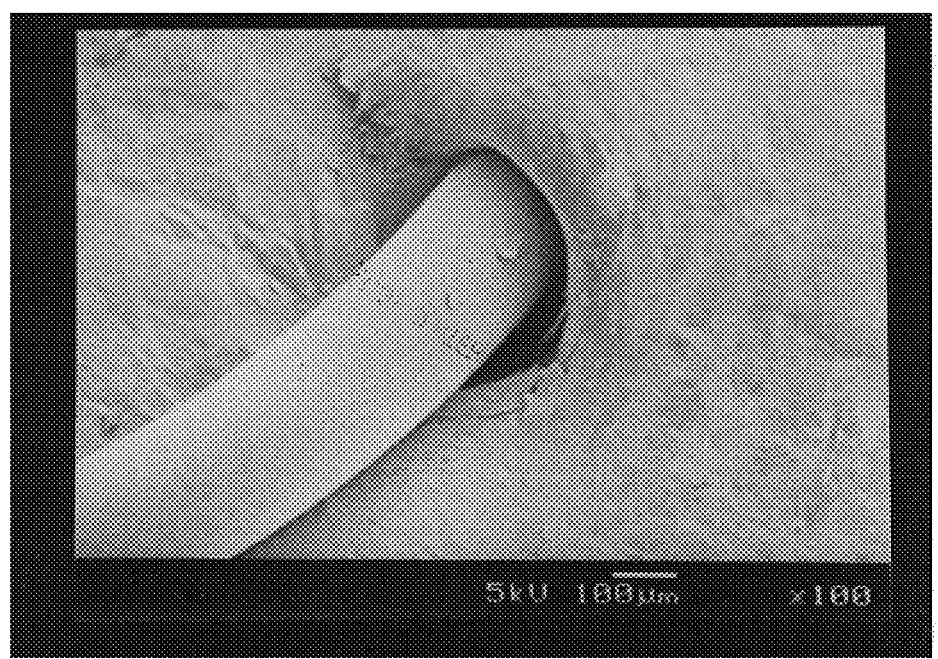
FIG. 4 is a photograph of a lyophilized cadaveric dura mater manufactured by Tokibo (Tutoplast Dura (registered trademark)).
Figure 5:
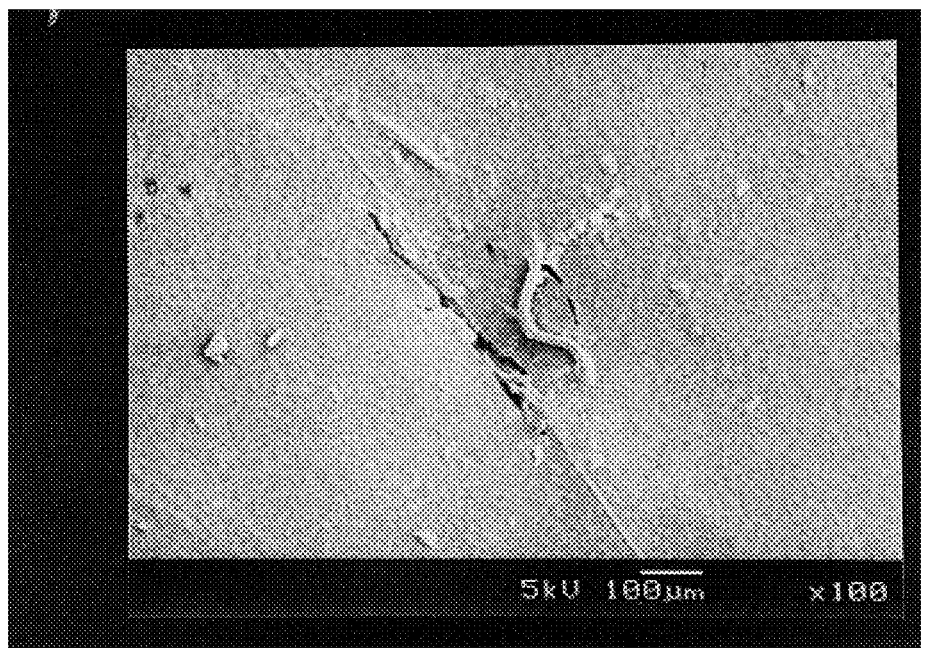
FIG. 5 is a photograph showing a state where the suture is pulled out from the artificial dura mater of the invention obtained in Example 1.
Figure 6:
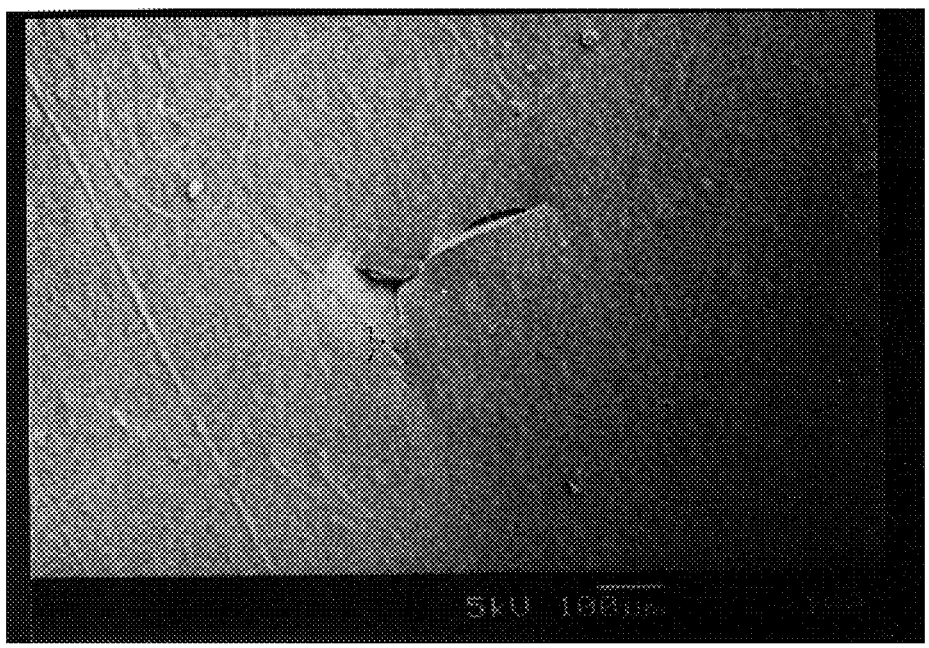
FIG. 6 is a photograph showing a state where the suture is pulled out from the artificial dura mater of the invention obtained in Example 2.
Figure 7:
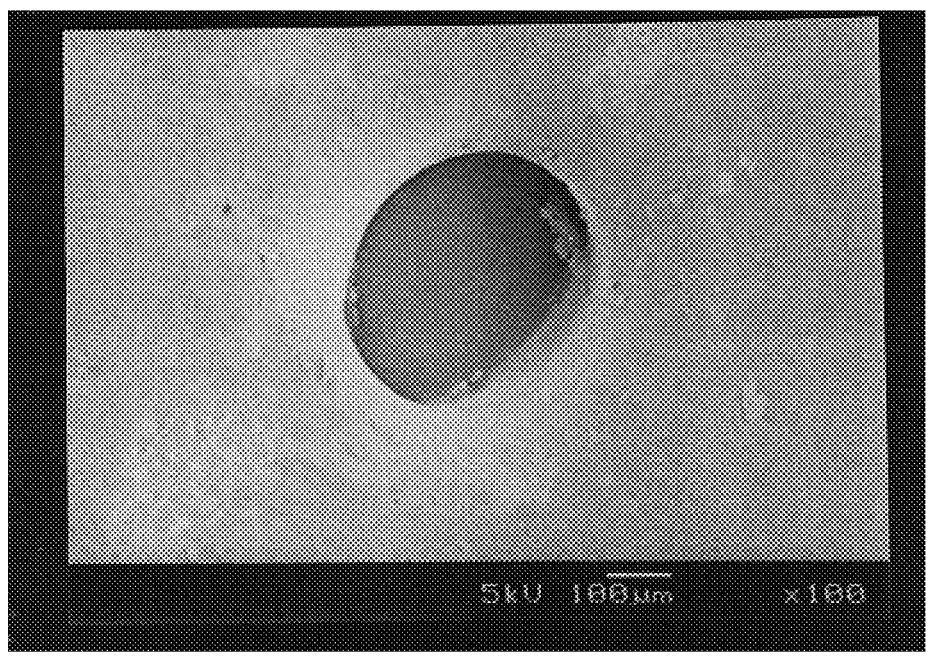
FIG. 7 is a photograph showing a state where the suture is pulled out from the e-PTFE manufactured by W. L. Gore & Associates, Inc. (GORE-TEX (registered trademark)).
Figure 8:
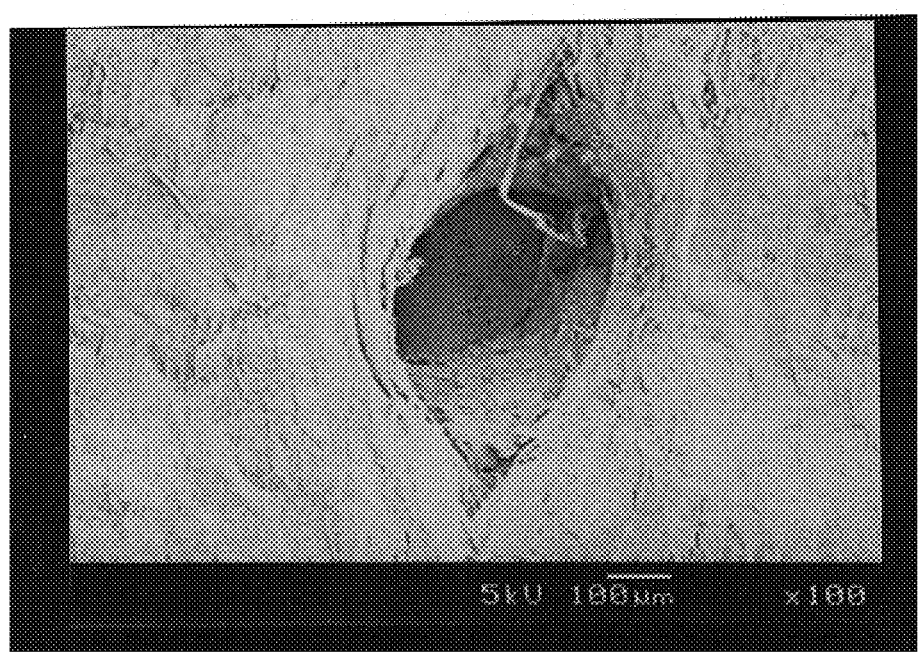
FIG. 8 is a photograph showing a state where the suture is pulled out from the lyophilized cadaveric dura mater manufactured by Tokibo (Tutoplast Dura (registered trademark)).

The present invention provides an artificial dura mater characterized by comprising at least a sheet of a biodegradable and bioabsorbable synthetic polymer and having a storage elastic modulus of $1 \times 10^7$ to $5 \times 10^8$ (Pa) at ordinary temperature.

The present invention further provides a process for producing an artificial dura mater by dissolving a lactide/ε-caprolactone copolymer (in a molar ratio ranging from 40/60 to 60/40) in a solvent, filtering the resultant solution and casting the same followed by air drying.

Moreover, the present invention provides a process for producing an artificial dura mater comprising the steps of:
(1) preparing a sheet by dissolving a lactide/ε-caprolactone copolymer (in a molar ratio ranging from 40/60 to 60/40) in a solvent, filtering the resultant solution and casting the same, followed by air drying and
(2) obtaining an artificial dura mater having a three layer structure prepared by integrally molding by vacuum press the sheets prepared by the step (1) and a reinforcement comprising a biodegradable and bioabsorbable polymer different from that of the sheet after sandwiching the reinforcement between the sheets.

Furthermore, the invention provides a method for treating a dural defect comprising suturing together the residual native dura mater and an artificial dura mater to cover the dural defect section.

According to the present invention, examples of the biodegradable and bioabsorbable synthetic polymer are aliphatic polyesters (polyglycolic acid, polylactic acid, polycaprolactone, polyvalerolactone and copolymers thereof), polyesterether (poly-1,4-dioxanone-2-one, poly-1,5-dioxepan-2-one, ethyleneglycol-said aliphatic polyester copolymer, propyleneglycol-said aliphatic polyester copolymer) and copolymers of the aliphatic polyester and polyesterether, preferably a copolymer of lactic acid (L form, D form, D,L form) and caprolactone, more preferably a copolymer of L-lactic acid and ε-caprolactone.

Preference is given to the lactic acid/caprolactone copolymer since the dynamic property and rate of degradation thereof can be easily controlled. Preferable molar ratio between the lactic acid and caprolactone in the copolymer ranges from 40/60 to 60/40. If the molar ratio of the lactic acid exceeds 60%, the resultant copolymer will be too rigid. Also, if the molar ratio of the caprolactone exceeds 60%, the resultant copolymer will be too rigid to be used as an artificial dura mater since it is liable to damage the brain surface.

An artificial dura mater of the invention may preferably have a tensile break strength of 4–20 MPa, Young's modulus at 10% extension of 9–40 MPa, flexural hysteresis of 0.05–1 gfcm/cm and flexural rigidity of 0.1–2 gfcm$^2$/cm are preferred in the invention.

If the tensile break strength is lower than 4 MPa, the resultant dura mater can not endure the intracranial pressure; therefore, the tensile break strength is at least 4 MPa, preferably 4–20 MPa.

Artificial dura maters having the Young's modulus at 10% extension of lower than 9 MPa, the extension of the flexural hysteresis of lower than 0.05 gfcm/cm, or the flexural rigidity of lower than 0.1 gfcm$^2$/cm are difficult to produce. Artificial dura maters having the Young's modulus at 10% extension of higher than 40 MPa, the flexural hysteresis of higher than 1 gfcm/cm, or the flexural rigidity of higher than 2 gfcm$^2$/cm are so rigid that the brain surface will be damaged.

In addition, the tensile elongation at break and the suture strength may preferably be 30–150% and 1.5–5.0 kgf/mm, respectively. If the tensile elongation at break is lower than 30%, the resultant dura mater will break due to the insufficient extensibility when subjected to a suturing under tension. If the tensile elongation at break is higher than 150%, the resultant artificial dura mater will be of too much extensibility resulting in leakage of fluid when a pressure is applied thereto and handling difficulties may arise when it is subjected to a suturing under tension because of the too much extensibility.

If the suture strength is lower than 1.5 kgf/mm, it is difficult for the resultant artificial dura mater to form a water-tight seal and, further, it may split from the suture penetration portion (pinhole) to cause leakage. Accordingly, the suture strength may be 1.5 kgf/mm or higher, preferably 1.5–5.0 kgf/mm.

In a case where the reinforcement prepared by a polyglycolic acid nonwoven fabric is used in the invention, the resultant artificial dura mater degrades more rapidly than that comprised of a single film since the reinforcement is hydrolyzed in a short period of time after embedded prior to the sheet portion and become a lattice-like film, thereby reducing the strength of the artificial dura mater. To the contrary, from the view point of a nonwoven fabric, the degradation speed of the polyglycolic acid nonwoven fabric is slower than a sheet comprised solely of the polyglycolic acid nonwoven fabric because the polyglycolic nonwoven fabric used in the invention is covered with the sheets. The structure is necessary for maintaining the suture strength of the artificial dura mater. Further, the increase in degradation speed of the artificial dura mater means that the artificial dura mater can be bioabsorbed as soon as the necessity for dural substitute is obviated to reduce the stress imposed in vivo.

In addition, the degradation speed can be changed within a certain range by changing the amount of the reinforcement. Further, according to the invention, if the reinforcement is comprised of a copolymer of a lactic acid and caprolactone, the artificial dura mater can be employed for a long-term embedment because the degradation speed of the reinforcement is substantially the same with that of the sheet portion.

In the present invention, the product may vary depending on an extensibility of the reinforcement provided that the extensibility of the reinforcement is lower than that of the sheets. A synthetic sheet having a flexibility sufficient to be used as an artificial dura mater typically are too high in the extensibility. Therefore, such synthetic sheet extends too much when a tension is applied thereto or, when a force is applied thereto during suture, it deforms to hinder a suture needle to penetrate. In this invention, the suppression of the extensibility of the artificial dura mater is achieved by way of the reinforcement, which means that the artificial dura mater of the invention is satisfactorily usable when sutured in an actual operation.

In a case where a stretchable knitted/woven fabric is used as the reinforcement, the artificial dura mater comprising the reinforcement is provided with the stretchability to be suitably used as a prosthesis for a moving part.

In the artificial dura mater of the invention, if the storage elastic modulus at ordinary temperature is higher than $5 \times 10^8$, the artificial dura mater will be so rigid as to damage the brain surface. If it is lower than $1 \times 10^7$, the artificial dura mater will be so flexible resulting in the handling difficulty. If a ratio between a loss elastic modulus and a storage elastic modulus of an artificial dura mater exceeds 0.2, a significant plastic deformation occurs to undesirably allow a pinhole when passing through a suture needle, which may lead to a leakage of cerebrospinal fluid.

The artificial dura mater of the invention may have a leakage ratio from a penetration portion of a suture, which is measured in a state where the suture being withheld after passing it through the dura mater (JIS L1092 (water resistant test) method A), of 10% or less (initial pressure: 50 mmHg for 60 min), preferably 5% or less, more preferably 3% or less, further more preferably 2% or less, most preferably 1.5% or less, especially 1.1% or less.

The artificial dura mater of the invention may have a thickness of 50–800 μm, preferably 100–300 μm. In a case where the artificial dura mater has the three-layer structure, a thickness of respective sheets on both of outer surfaces may be 25–400 μm, preferably 50–150 μm. The reinforcement may have a thickness of 20–500 μm, preferably 50–200 μm.

The lactic acid-caprolactone copolymer may have a weight average molecular weight of about 100,000–500,000, preferably about 150,000–300,000. Polyglycolic acid may have an intrinsic viscosity of about 0.8–1.8, preferably about 1.0–1.4.

The sheet of biodegradable and bioabsorbable synthetic copolymer which constitutes the artificial dura mater of the invention, especially, the sheet comprising the lactic acid-caprolactone copolymer may preferably have smooth surfaces free of roughness. Such sheet can be obtained by dissolving the lactic acid-caprolactone copolymer in a solvent, filtering the resultant solution, and then casting the same, followed by air-drying.

Since the sheet of the invention comprising the lactic acid-caprolactone copolymer which is prepared by the casting method is a sheet having smooth surfaces free of roughness, no gap occurs around a suture as shown in FIG. 1 and, therefore, the sheet is substantially free of leakage.

According to the invention as explained above, there can be provided an artificial dura mater improved of its qualities such as leakage and suture strength and a process for producing the same.

BEST MODE FOR CARRYING OUT THE INVENTION

The following examples serve to illustrate the present invention. It is to be understood that the examples are not restrictive of the present invention.

In addition, "JIS L1092 method A" is a water resistant test conducted by way of water pressure method.

EXAMPLE 1

1. Production of Polymer
(1) Film (Sheet)

L-lactide/ε-caprolactone copolymer [molar ratio: 50/50; weight average molecular weight by GPC: 220,000; hereinafter referred to as P (L-LA/CL) (molar ratio: 50/50) was synthesized in a conventional manner.

(2) Reinforcement (Nonwoven Fabric)

Polyglycolic acid (intrinsic viscosity=1.26) was produced in a conventional manner.

2. Production of Film (Sheet)

1. P (L-LA/CL) (molar ratio: 50/50) obtained in (1) was dissolved in a solvent (chloroform) so that the resultant solution contains 5 wt % of P (L-LA/CL) (molar ratio: 50/50). After completion of dissolution, the solution was filtered to remove insoluble matter. The solution was then casted on a glass plate and subjected to an air drying, followed by a vacuum drying at 50° C. for 12 hours to remove the solvent.

3. Production of Reinforcement (Nonwoven Fabric)

1. A nonwoven fabric was produced by spinning the polyglycolic acid obtained in (2) to obtain a polyglycolic acid yarn having about 20 deniers followed by drawing, and then circular knitting the drawn yarn and needle punching this knitting.

4. Composite

An artificial dura mater having a three-layer structure (film thickness of 200 μm) was produced by integrally molding the reinforcement (nonwoven fabric) obtained in (3) with the films (sheets) obtained in (2) placed at both sides of the reinforcement by vacuum press at a temperature of 140° C. and a pressure of 50 kg/cm$^2$.

EXAMPLE 2

P (L-LA/CL) film (film thickness of 200 μm) was produced by superimposing the films (sheets) obtained in Example 1-(1) and integrally molding the superimposed films by vacuum press at a temperature of 140° C. and a pressure of 50 kg/cm$^2$.

EXAMPLE 3

A three-layer film (thickness of 250 μm) was produced by sandwiching the reinforcement (nonwoven fabric) obtained in Example 1–3 between the sheets (films) obtained in (2), and integrally molding them by vacuum press at a temperature of 120° C. and a pressure of 10 kg/cm$^2$ in such a manner that the nonwoven fabric be not embedded in the sheets.

(Leakage Test)

Test pieces of the artificial dura maters of the invention obtained in Examples 1 and 2, e-PTFE manufactured by W. L. Gore & Associates, Inc. (GORE-TEX (registered trademark)) and a lyophilized cadaveric dura mater manufactured by Tokibo (Tutoplast Dura (registered trademark)), each of which was penetrated by a 3-0 monofilament nylon suture using a ½ circle taper point, were employed. With the suture being held at the penetration portions, the test was conducted in accordance with JIS L1092 (water resistant test) method A (low water pressure method). Specifically, after each of the test pieces was clamped in a state where the suture passed therethrough, the water level of a level gage was elevated up to 70 cm, and then water levels after predetermined time periods were measured. The results are shown in Table 1. Since water leaked only from the penetration portion (pinhole), the results are not indicated as leakage per unit area. The measurement temperature was 37° C.

TABLE 1

| | Sample | | | | | | | |
|---|---|---|---|---|---|---|---|---|
| | Example 1 | | Example 2 | | e-PTFE | | Cadaveric Dura Mater | |
| Time (min) | Water level (cm) | Leakage (%) | Water level (cm) | Leakage (%) | Water level (cm) | Leakage (%) | Water level (cm) | Leakage (%) |
| 1 | — | — | — | — | 44.2 | 36.9 | 66.7 | 4.7 |
| 2 | — | — | — | — | 26.2 | 62.6 | 64.3 | 8.1 |
| 3 | — | — | — | — | 12.5 | 82.2 | 62.0 | 11.4 |
| 5 | — | — | — | — | 2.8 | 96.0 | 57.7 | 17.6 |
| 10 | 69.9 | 0.2 | 69.7 | 0.4 | — | — | 50.1 | 28.4 |
| 20 | 69.7 | 0.4 | 69.6 | 0.6 | — | — | 38.1 | 45.6 |
| 30 | 69.6 | 0.5 | 69.5 | 0.7 | — | — | 29.2 | 58.3 |
| 60 | 69.2 | 1.1 | 69.2 | 1.1 | — | — | 14.2 | 79.7 |

As shown in Table 1, the leakages (%) of the test pieces of Examples 1 and 2 were both 1.1% even after 60 minutes whereas the leakage of e-PTFE (GORE-TEX (registered trademark)) after 5 minutes was 96.0% and the leakage of the lyophilized cadaveric dura mater (Tutoplast Dura (registered trademark)) after 60 minutes was 79.7%. It is apparent that the present invention is excellent in leakage resistance.

In addition, FIGS. 1–4 are electron microscopic photographs showing the test pieces, after being penetrated by a suture with a needle, each holding the suture at the penetration portion (in a state where a suture passes through each of the test pieces).

(Tensile Test, Suture Strength, Restoring Strength)

(1) Tensile Test

The artificial dura maters obtained in Examples 1–3 in the present invention were cut into test pieces each having a size of 1×8 cm. A tensile test was conducted under the conditions of a chuck distance of 5 cm and a stress rate of 100 mm/min.

Also, elongation at break of the test pieces were measured under the same conditions.

(2) Suture Strength

The artificial dura maters of the invention obtained in Examples 1 and 2 were cut into test pieces each having a size of 1×4 cm. The test pieces each was penetrated with 3-0 nylon monofilament suture using a ½ circle taper point at 3 mm from the edge, and then the suture strengths were measured by conducting a tensile test under the conditions of a chuck distance of 10 cm and a stress rate of 100 mm/min.

(3) Flexural Test

The artificial dura mater of the invention obtained by Examples 1 and 2 were cut into test pieces each having a size of 1×8 cm to measure the flexural rigidity and flexural hysteresis by means of a pure bending tester (KES-FB2).

Results of the (1) to (3) are shown in Table 2.

TABLE 2

| | Example 1 | Example 2 | Example 3 |
|---|---|---|---|
| Tensile Break Strength (MPa) | 13.1 | 11.4 | 9.2 |
| Elongation at Break (%) | 76.6 | 253.9 | 138.2 |
| Young's modulus at 10% extension (MPa) | 19.2 | 2.1 | 7.6 |
| Suture Strength (kgf/mm) | 4.73 | 0.35 | 1.89 |
| Flexural Rigidity (gfcm$^2$/cm) | 0.774 | 0.223 | 0.346 |
| Flexural Hysteresis (gfcm/cm) | 0.251 | 0.205 | 0.173 |

Example 1 (reinforced by the nonwoven fabric) is higher in the tensile break strength than Example 2. However, the elongation at break of the Example 1 is ⅓ of that of Example 2, which is close to a human dura mater. Example 3 is almost the same with Example 2 in the absolute value of tensile break strength, and the elongation at break thereof is twice that of Example 1 in spite of the use of nonwoven fabric. Thus, it is observed that the extensibility of an artificial dura mater can be controlled by inserting between sheets (films) a nonwoven fabric having a certain extensibility or by changing the degree of integration.

Further, it is noted that Example 1 is superior in all the characteristic values to Example 2.

(Storage Elastic Modulus)

Storage elastic modulus of samples of Examples 1 and 2 as well as of the e-PTFE (GORE-TEX (registered trademark)) were measured by means of "RHEOVIBRON" DDV-11-EA based on the non-resonant forced vibration method under the conditions of a frequency of 11 Hz and a temperature of 37° C.

The results are shown in Table 3.

TABLE 3

|  | Sample | | |
| --- | --- | --- | --- |
|  | Example 1 | Example 2 | e-PTFE |
| Elastic Modulus (Pa) (Storage Elastic Modulus) | $2.1 \times 10^8$ | $2.5 \times 10^7$ | $1.1 \times 10^7$ |
| Loss Elastic Modulus (Pa) | $1.4 \times 10^7$ | $1.8 \times 10^6$ | $3.1 \times 10^6$ |
| Loss Elastic Modulus/Storage Elastic Modulus | 0.066 | 0.077 | 0.299 |

From the results of the elastic modulus, it is apparent that the artificial dura mater of the present invention has a satisfactory elasticity in the range of the temperatures wherein typical medical instruments are used, and that is resistant to plastic deformation caused by external force. The results of the leakage test and the photographs of pinholes (FIGS. 1 and 2) reveal that the Examples 1 and 2 are both resistant to plastic deformation.

(Hydrolysis Property Test)

(1) Strength Test

Products of Example 1, Example 2 and Example 3 of the present invention respectively were cut into test pieces each having a size of 1×8 cm. The test pieces were immersed in a saline at 37° C. and then taken out after a predetermined time period. Tensile test was conducted by using a tensilometer under the conditions of a chuck distance of 5 cm and a stress rate of 100 mm/min to measure strength changes. The results are shown in Table 4.

(2) Weight Test

Test pieces were prepared by cutting 1 g off from each product of Example 1, Example 2 and Example 3 of the invention. The test pieces were immersed in a saline at 37° C. and then taken out after a predetermined time period to be dried in a vacuum dryer at ordinary temperature overnight. Weights of the dried test pieces were measured to detect weight changes. The results are shown in Table 5.

In both of the tensile test and residual weight test, the integral-molding type sample was decomposed most rapidly. Example 3 behaved similarly to Example 1 in the early stages of the tests, but in the late stages, it behaved similarly to Example 2. In view of the above, the initial characteristics and the decomposition period can be controlled by the presence or absence of the reinforcement and the form of integration.

TABLE 4

Results of Hydrolysis Property Test (Tensile Strength (MPa))

|  | Sample | | |
| --- | --- | --- | --- |
| Time (weeks) | Example 1 | Example 2 | Example 3 |
| 0 | 7.4 | 7.7 | 6.5 |
| 1 | 5.7 | 7.8 | 6.0 |
| 4 | 3.7 | 5.7 | 4.6 |
| 8 | 2.6 | 3.5 | 3.1 |
| 12 | 1.6 | 2.1 | 1.9 |
| 16 | non-recoverable | 1.1 | 1.0 |
| 20 |  | non-recoverable | non-recoverable |

TABLE 5

Results of Hydrolysis Property Test by Weight (g)

|  | Sample | | |
| --- | --- | --- | --- |
| Time (weeks) | Example 1 | Example 2 | Example 3 |
| 0 | 1.00 | 1.00 | 1.00 |
| 4 | 0.99 | 0.98 | 0.98 |
| 8 | 0.95 | 0.99 | 0.95 |
| 12 | 0.94 | 0.98 | 0.93 |
| 16 | 0.88 | 0.94 | 0.92 |
| 20 | 0.69 | 0.88 | 0.85 |
| 24 | 0.23 | 0.78 | 0.70 |
| 30 | non-recoverable | 0.32 | 0.33 |
| 36 | non-recoverable | non-recoverable | non-recoverable |

What is claimed is:

1. A process for producing an artificial dura mater having a three-layer structure comprising:
   (a) preparing an artificial dura mater sheet by:
      (i) dissolving a lactide/ε-caprolactone copolymer in a solvent to form a solution wherein the molar ratio of the copolymer is from about 40/60 to about 60/40;
      (ii) filtering the solution;
      (ii) casting the solution;
      (iv) air-drying the solution to remove the solvent; and
      (v) vacuum-drying the solution to remove the solvent, wherein an artificial dura mater sheet is formed;
   (b) repeating (a) to form two more artificial dura mater sheets;
   (c) placing a reinforcement of a biodegradable and bioabsorbable synthetic polymer different from the copolymer of (a) (i) between the artificial dura mater sheets produced in (a) and (b) to form a sandwich; and
   (d) vacuum pressing the sandwich to integrally mold the artificial dura mater sheets the reinforcement, wherein an artificial dura mater is produced.

2. The process of claim 1, wherein the artificial dura mater sheet comprising a lactide/ε-caprolactone copolymer has a storage elastic modulus at 37° C. of from about $1 \times 10^7$ Pa to about $5 \times 10^8$ Pa.

3. The process of claim 1, wherein the artificial dura mater sheet comprising a lactide/ε-caprolactone copolymer has a tensile elongation at break of from about 30% to about 150% and has a suture strength of 1.89–5.0 kgf/mm.

4. The process of claim 1 wherein the biodegradable and bioabsorbable synthetic polymer is selected from the group consisting of an aliphatic polyester, a polyesterether, a co-polymer of an aliphatic polyester and a polyesterether.

5. The process of claim 4 wherein the biodegradable and bioabsorbable synthetic polymer is selected from the group consisting of polyglycolic acid, polylactic acid, polycaprolactone, polyvalerolactone and copolymers thereof.

6. The process of claim 4 wherein the biodegradable and bioabsorbable synthetic polymer is selected from the group consisting of poly-1,4-dioxanone-2-one, poly-1,5-dioxepan-2-one, a copolymer of ethyleneglycol and an aliphatic polyester, and a copolymer of propyleneglycol and an aliphatic polyester.

7. The process of claim 4 wherein the biodegradable and bioabsorbable synthetic polymer is a copolymer of an aliphatic polyester and a polyesterether.

8. A process for producing an artificial dura mater sheet comprising:

dissolving a lactide/ε-caprolactone copolymer in a solvent to form a solution wherein the molar ratio of the copolymer is from about 40/60 to about 60/40;

filtering the solution;

casting the solution;

air-drying the solution to remove the solvent; and vacuum-drying the solution to remove the solvent, wherein an artificial dura mater sheet comprising a lactide/ε-caprolactone copolymer having a tensile elongation at break from about 30% to about 150% and having a suture strength of 1.89–5.0 kgf/mm is produced.

9. A process for producing an artificial dura mater comprising:

providing three artificial dura mater sheets each comprising a lactide/ε-caprolactone copolymer;

providing two reinforcement sheets of biodegradable and bioabsorbable synthetic polymer different from that of the sheets;

placing the reinforcement sheets between the artificial dura mater sheets to form a sandwich; and vacuum pressing the sandwich, wherein the artificial dura mater sheets are integrally molded with the reinforcement sheets and an artificial dura comprising a lactide/ε-caprolactone copolymer having a tensile elongation at break from about 30% to about 150% and having a suture strength of 1.89–5.0 kgf/mm is produced.

* * * * *